(12) United States Patent
Hagelauer

(10) Patent No.: US 8,414,472 B2
(45) Date of Patent: Apr. 9, 2013

(54) NAVIGATION FOR FOCUSED WAVE TREATMENT

(75) Inventor: Ulrich Hagelauer, Constance (DE)

(73) Assignee: Storz Medical AG, Tägerwilen (CH)

( * ) Notice: Subject to any disclaimer, the term of this patent is extended or adjusted under 35 U.S.C. 154(b) by 1115 days.

(21) Appl. No.: 12/338,770

(22) Filed: Dec. 18, 2008

(65) Prior Publication Data

US 2009/0156894 A1 Jun. 18, 2009

(30) Foreign Application Priority Data

Dec. 18, 2007 (EP) .................................... 07024516

(51) Int. Cl.
*A61B 1/00* (2006.01)
*A61B 1/04* (2006.01)
*A61B 6/00* (2006.01)
*A61M 37/00* (2006.01)
*A61N 2/00* (2006.01)

(52) U.S. Cl. ........ 600/104; 600/109; 600/117; 600/118; 600/12; 378/4

(58) Field of Classification Search ................... 600/104, 600/109, 117, 118, 120, 160, 11–13; 378/4
See application file for complete search history.

(56) References Cited

U.S. PATENT DOCUMENTS

| | | | |
|---|---|---|---|
| 4,896,673 A | 1/1990 | Rose et al. | |
| 4,955,385 A | 9/1990 | Kvalo et al. | |
| 5,938,603 A | 8/1999 | Ponzi | |
| 6,112,111 A | 8/2000 | Glantz | |
| 6,226,547 B1 | 5/2001 | Lockhart et al. | |
| 6,911,026 B1 | 6/2005 | Hall et al. | |
| 2002/0019644 A1 | 2/2002 | Hastings et al. | |
| 2002/0111386 A1* | 8/2002 | Sekins et al. ................ | 514/759 |
| 2004/0242995 A1 | 12/2004 | Maschke | |
| 2005/0113685 A1 | 5/2005 | Maschke et al. | |
| 2007/0135713 A1 | 6/2007 | Borgert et al. | |
| 2007/0225559 A1 | 9/2007 | Clere et al. | |

FOREIGN PATENT DOCUMENTS

| | | |
|---|---|---|
| CA | 2 555 473 | 9/2005 |
| DE | 41 15 447 A1 | 11/1992 |
| DE | 196 22 920 A1 | 12/1997 |
| DE | 103 13 868 A1 | 10/2004 |
| DE | 103 54 496 A1 | 7/2005 |
| EP | 0 382 392 | 8/1990 |
| FR | 2 686 499 | 7/1993 |
| JP | 01-151450 | 6/1989 |
| WO | WO 01/03589 A1 | 1/2001 |
| WO | WO 2007/079352 A2 | 7/2007 |

OTHER PUBLICATIONS

Abstract of JP 01-151450, Jun. 14, 1989, Olympus Optical Co Ltd.
English translation of Official Communication of the EPO of Apr. 15, 2008, communicating the European Search Report for priority European Application No. 07 024 516.2.

* cited by examiner

*Primary Examiner* — Rochelle-Ann J Blackman
(74) *Attorney, Agent, or Firm* — Wood, Phillips, Katz, Clark & Mortimer

(57) ABSTRACT

The invention generally relates to apparatuses and methods for shock wave treatment of the human body. In particular, the invention relates to navigational aspects of the shock wave treatments, including apparatuses and methods which enable accurate focusing of shock waves.

25 Claims, 3 Drawing Sheets

NAVIGATION FOR FOCUSED WAVE TREATMENT

BACKGROUND

Shock waves, i.e. mechanical waves sometimes also named "acoustic", are presently used in different ways for therapeutic treatment. Shock wave lithotripsy is especially important and has been the starting point of the development in a historical sense, namely the disintegration of concrements in the body, especially stones, using focused shock waves of high amplitude and steep rising edges. Normally, single pulses are directed to the concrement, wherein the first "half wave" corresponding to a compression dominates as regards edge steepness and amplitude whereas already the next succeeding half wave, corresponding to an expansion, is substantially less pronounced. Such pulses are used in a regularly repeated manner.

Comparable methods using shock waves are also known for other indications, e.g. for treating badly healing bone fractures.

The essential frequencies of the above-mentioned therapies are above the acoustic threshold; thus, these therapies are ultrasonic methods.

Although therapies using non-focused shock waves are known, the present invention is related to applications of focused waves (including pulses, compare above). Although the delimitation between focused and non-focused waves can be problematic, in the following, only such therapies shall be meant in which the shock waves are intentionally concentrated to a body region which is more or less extended in order to increase intensities, pressures or edge steepnesses.

Since in these focusing therapies the localization to the body region to be treated is essential, the adjustment of the respective apparatus for a correct positioning of the focus region in the body is of essential importance. This relates to a preliminary adjustment to the region to be treated, e.g. a stone, on the one hand. In case of too large tolerances, healthy tissue is damaged or unnecessarily much of healthy tissue is subjected to the therapy and, further, the success of therapy in the region to be treated is diminished or endangered. The term "navigation" is used here.

As a complication, further, the navigation does not necessarily need to be a static operation, i.e. changes during treatment may occur. Movements of the patient or displacements of organs, especially due to respiration, are an essential cause.

Image producing methods can be used for navigation that render the region to be treated distinguishable from surrounding regions and produce navigation information, i.e. coordinates, for the shock wave apparatus. Particularly known is a running X-ray monitoring during shock wave lithotripsy. Since at least two X-ray projections are necessary for the determination of the spatial position, a substantial technical effort for tilting X-ray axes and corresponding costs are caused. As regards the patient, X-ray monitoring leads to radiation exposure.

SUMMARY OF THE INVENTION

According to one embodiment of the invention, an apparatus is provided, wherein said apparatus comprises: a shock wave source adapted to produce said shock waves, a focusing device adapted to focus said shock waves onto a focus region in said body to be treated, a locating probe adapted to be inserted into said body to be treated, a magnetic locating element as a part of said locating probe and arranged in said locating probe, and a magnetic locating apparatus adapted to locate said magnetic locating element in said body to be treated and thus adapted for navigation during said treatment.

Further, the invention is directed to a respective method in which the apparatus is used.

In addition, the invention also relates to shock wave therapies using proper waves, i.e. continuously oscillating waves. They can be used in a focused manner for heating body tissue, e.g. for the so-called thermal ablation of tumors.

Preferred embodiments of the apparatus according to the invention and its use are given in the dependent claims. The features therein as well as the disclosure in the description hereunder are to be understood in view of all categories of the invention although differences there between will not be made explicitly as regards the details. The invention also includes navigation methods and treatment methods.

In one embodiment, the basic idea of the invention is to use a combination of a locating probe and a magnetic locating system. The locating probe is a minimally invasive instrument for insertion into the body, namely near to the region to be treated, however, not necessarily adjacent to this region. Preferably, a catheter or an endoscope can be chosen, wherein the different terms shall mean that a catheter has no optical vision device and an endoscope comprises an optical vision device. Thus, the endoscope can also be flexible and the catheter can also be rigid, at least principally.

Magnetic locating systems are known and are commonly used as tracking systems. In the body, a locating element is arranged which could be an active or a passive coil or even a permanent magnet. This locating element can be located by an extracorporeal magnetic locating apparatus and its position (i.e. coordinates) can be determined. According to the invention, the magnetic locating system serves to navigate the shock wave apparatus, i.e. the shock wave apparatus is calibrated with reference to the coordinate information of the magnetic locating system.

According to the invention, the magnetic locating element is arranged within the locating probe, preferably within its tip or near its tip. Thus, it is arranged near the region to be treated. Then, the distance between the magnetic locating element and the region to be treated can be determined or defined in various ways. This includes measuring the distance in case that the magnetic locating element is not adjacent to or in contact with the region to be treated, as well as a minimization of the distance to a quantity without relevance for therapy, i.e. an arrangement of the locating element adjacent to the region to be treated. The criterion for the relevance of the minimized distance is the focus region of the shock waves. Thus, the basic assessment is that in case of a sufficiently close arrangement of the magnetic locating element to the region to be treated, the remaining difference in position is irrelevant for the shock wave therapy so that the position of the magnetic locating element can be used as the "target" for the navigation. In other cases, the remaining distance is measured and considered by means of a calculation.

The magnetic locating system provides a cost-effective and, as regards the patient, careful and gentle navigation system. The calibration according to the invention using the locating probe is also economic as regards the equipment and cost-effective as well as time-efficient for the therapeutic procedure, practical, and free of radiation exposure. Further, minimally invasive locating probes as catheters and endoscopes are not connected with substantial burden on the patient.

Thus, one advantage of the invention is that it allows to replace the X-ray navigation with a navigation based on the magnetic locating. However, apparatuses and methods of the invention can also be combined with X-ray imaging in an advantageous manner. Thus, in one embodiment, the invention relates to a combination of the navigation based on the magnetic locating with an X-ray based navigation.

If a combination of the navigation techniques is used, the X-ray imaging would usually provide a preliminary and thus preferably only single image for calibration purposes together with the locating probe. The invention allows for the running monitoring and especially the consideration of patient movements independently from X-ray monitoring. In certain embodiments of the invention, X-ray technology can be totally dispensed with, thus substantially reducing the expenditure in equipment and substantially simplifying the procedure for the clinic staff. Finally, embodiments of the invention exist in which, although X-ray imaging is used, it is simplified in that only one single imaging axis is used and complicated tilting mechanisms can be dispensed with.

Thus, the invention provides for an effective, simple and economical shock wave navigation.

In one embodiment of the invention, the locating probe is an endoscope and thus comprises an optical vision device. Therewith, the approaching of the endoscope, especially the endoscope tip, onto the treatment region can be controlled visually. For example, the endoscope can be introduced via the urethra and pushed forward until a kidney stone to be treated becomes visible in the patient. By means of the guidance of the endoscope due to the visual control, a spatial correspondence between endoscope and stone or between endoscope and the treatment region can be established. In the simplest case, the endoscope can be approached to the stone so that the magnetic locating element, e.g. a coil in the endoscope tip, is directly positioned beside the stone. As soon as the magnetic tracking system detects the position of the magnetic locating element, it can actually monitor the positions of the stone as well, as long as the direct neighborhood between the magnetic locating element and the stone is conserved. This can be certified by visual control. X-ray imaging or other imaging technologies using extracorporeal imaging apparatus are not necessary, however, they can be used preliminary in order to increase the safety of diagnosis.

Depending on the technical implementation of the endoscope and the precise manner of shock wave treatment, it may be problematic to leave a part of the endoscope in the focus region during the shock wave treatment. For example, the focus regions of shock wave lithotripsy apparatus may damage classical rigid endoscopes. Thus, another embodiment of the invention is provided, in which the endoscope comprises a distance measuring device. Preferred are optical distance measuring methods, i.e. the methods using light. Some examples include stereoscopic, holographic, or propagation time measurement methods allowing a quantitative measurement of the distance between the endoscope, e.g. the endoscope tip, and for example a stone. The distance measured can be accounted for in the navigation and thus provides a correction of the target area as detected by the magnetic locating apparatus.

A further embodiment of the invention uses a catheter within the measurement endoscope and approaches the endoscope as described above into the neighborhood of the treatment region under visual control. The direct neighborhood of endoscope and treatment region is, however, avoided due to the reasons named. Instead, a catheter comprising the magnetic locating element is pushed out of a working channel of the endoscope and positioned such that the magnetic locating element itself is arranged in direct neighborhood of the treatment region. The catheter can be less sensitive to shock waves and/or be a disposable product. The control of the direct neighborhood between the treatment region and the catheter or, in an embodiment mentioned above, the endoscope in the final phase may also be manual/sensory, naturally beside a visual control, for example by sensing the contact to the stone manually.

As already mentioned, the invention can be combined in an advantageous manner with an X-ray apparatus. This is true more generally for extracorporeal imaging techniques, e.g. ultrasonic diagnosis.

In particular, such imaging can verify the approach between magnetic locating element and treatment region already done by visual control, possibly using a distance measurement. In case of a catheter without visual device, an imaging method can replace the visual control. Thus, the catheter can be arranged so that the image shows a direct neighborhood to the treatment region or how large the remaining distance is in order to consider it as a correction.

In a preferred embodiment, the invention relates to a combination of a catheter as a locating probe with imaging in the following way: An X-ray image or another extracorporeal image having a comparable imaging axis is used for positioning the magnetic locating element in the catheter in a plane perpendicular to the imaging axis. In the direction of the imaging axis itself, the magnetic locating element is located only by the magnetic locating apparatus but not by a separate control of the neighborhood between the treatment region and the magnetic locating element. This is especially reasonable if, for other reasons, such as anatomy, sufficiently precise implications regarding this neighborhood in the direction of the imaging axis are possible. On the one hand, typical shock wave treatments have a lengthy focus region, the longitudinal extension of which is parallel to the main propagation direction of the shock waves. On the other hand, the anatomical situation can already predefine a more precise localization than the extension of this focus region. The localization by the extracorporeal imaging can be done by using a small angle to this shock wave propagation direction, as far as possible therein, so that the localization of the magnetic locating element relative to the treatment region detected with sufficient precision is in a direction in which the focus region is relatively long.

An essentially coaxial geometry is preferred therein, e.g. having the main axis of shock wave propagation substantially coincident with the X-ray axis. Namely, shock wave sources are preferred that have a hollow construction, e.g. a hollow coil of a lithotripsy source. Then, the X-ray imaging can be done through the hollow space and thus essentially produce an image in the plane of the shortest focus region extension. Therein, a slight inclination between the axes can occur, naturally, as the treatment region imaged by X-ray or generally by an extracorporeal technology need not necessarily be centered precisely in the image. Deviations from the center can be compensated by respective adjustments of the shock wave apparatus without a following adjustment of the X-ray apparatus. Thus, within the imaging region, inclinations of the axes can occur. In this embodiment of the invention the axes can also be coaxially arranged, however.

Further, the visual control, possibly in combination with the distance measurement described above, can be used for a positioning in the (X-ray) imaging direction itself, namely in the direction not visible by a single X-ray image. The visual control can also be used for the introduction of an endoscope into the relevant region. The additional safety and precision achieved by the extracorporeal imaging can be combined with a renunciation of a multitude of X-ray images.

However, if an X-ray apparatus providing for several imaging directions is available, the locating probe, especially as a simple catheter without visual device, can also be located by at least two X-ray images within the body in a three dimensional manner. In this localization, a possible residual distance to the treatment region can be measured by the imaging. Usually, such a measurement is superfluous because the catheter is brought into the direct neighborhood, anyway. One advantage of the invention includes the use of the magnetic tracking system for the following navigation, so that X-ray imaging is only necessary preliminarily.

In the various combinations with extracorporeal imaging techniques, the catheter must be visible for the extracorporeal imaging technique used. For example, inserts (markers) having an increased X-ray absorption can be used. The magnetic locating element itself can serve for this purpose as well. Endoscopes are usually very well visible, at least in case of rigid metal constructions. However, flexible locating probes low in X-ray contrast and having a visual device, e.g. by means of a flexible glass fiber bundle which are named "endoscope" according to the definition used here are considered as well. If this approach is used, a sufficient contrast in the X-ray image should be provided by the magnetic locating element or another marker.

The shock wave source is preferably extracorporeal. It can be coupled to the body by a liquid volume, e.g. within a bellow. Shock wave lithotripters are an especially important field of the invention.

BRIEF DESCRIPTION OF THE DRAWINGS

Hereunder, the invention will be explained in more detail by means of exemplary embodiments wherein the individual features can also be relevant for the invention in other combinations and refer to all categories of the invention implicitly, as already mentioned.

DETAILED DESCRIPTION OF THE INVENTION

Figure 1:
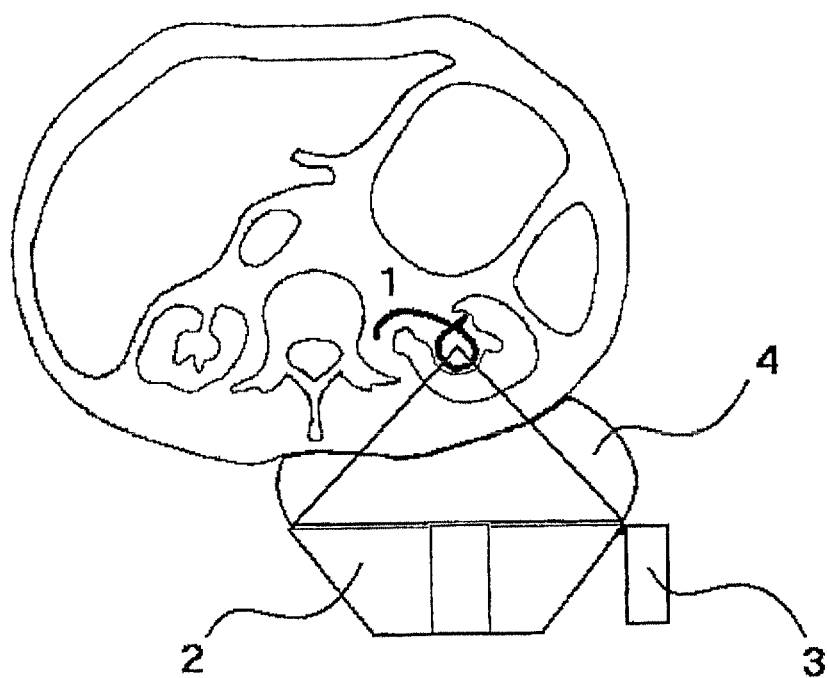
FIG. 1 shows a schematic view of an apparatus according to the invention and a section through a human abdomen.

FIG. 1 shows a schematic section through the abdomen of a human in the upper region of the figure. In the lower region, the spinal column and a respective kidney on the right side and on the left side thereof can be seen. The right kidney in the figure contains a catheter 1 having a so-called double J form. Catheter 1 contains one or several metallic magnetic coils in its most distal portion shown, serving as a magnetic locating element on the one hand and providing a good X-ray contrast on the other hand.

Particularly in case of urological stones, the introduction of the catheter is advantageous to avoid a blocking of draining vessels by stone fragments and to guarantee a draining of urine through the catheter independently from the transport path of the stone fragments.

A magnetic locating apparatus 3 shown in the lower right region can detect the position of the magnetic coils. In this exemplary embodiment, it is fastened to a shock wave apparatus 2 known as such having integrated focusing devices and coupled to the body by a liquid-filled bellow 4. The lines converging from the shock wave apparatus 2 through the liquid volume in bellow 4 to a point in the loop of catheter 1 symbolize the focused shock waves from source 2. Thereby, a kidney stone shall be disintegrated which is positioned in the focus region indicated.

Catheter 1 is preliminarily introduced through the urethra and displaced to the relevant region of the kidney in a manner known as such. There, it can be positioned by a conventional series of X-ray images or verified in its position. Hereto, several known methods of fluoroscopy or radiography are adequate. Finally, it is known from the X-ray images that catheter 1 is arranged such that the magnetic coils are adjacent to the stone. Thus, the magnetic coils serve for marking the stone position, namely both in the X-ray image and in the magnetic tracking.

Since magnetic locating apparatus 3 and shock wave apparatus 2 are mounted in a fixed spatial relationship with reference to each other, the positional data of the magnetic tracking system can be used directly as target coordinate data for shock wave apparatus 2 under consideration of this spatial relationship. Thus, the shock wave focus can be adjusted onto the stone as well, e.g. by turning or displacing a structural unit to which shock wave apparatus 2 and magnetic locating apparatus 3 are mounted. Simultaneously, the spatial relationship between the shock wave focus and the magnetic coil positions can be displayed numerically and/or graphically. As soon as a sufficiently precise coincidence is achieved, the shock wave treatment as such can start.

During this treatment, magnetic tracking system 3 continuously monitors the position of the magnetic coils. In case of movements of the patient or a change of the magnetic coil positions due to other circumstances, the treatment can be interrupted and can be continued after a recalibration.

Figure 2:
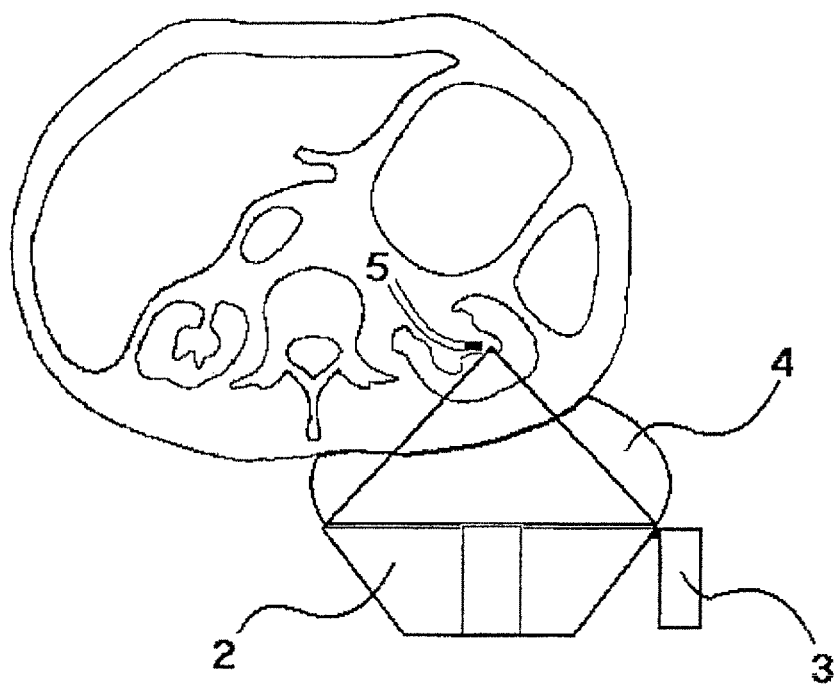
FIG. 2 shows a similar view as in FIG. 1, however of a second embodiment.

The second embodiment in FIG. 2 differs from the first embodiment of FIG. 1 as regards the locating probe, first. Here, an endoscope 5 is introduced such that the endoscope tip shown in a dark manner in the figure is arranged near the focus region of shock wave apparatus 2. The endoscope is a rigid tubular construction having an optical vision device for the operator. Therewith, the process of introduction can already be controlled optically, e.g. in choosing the right way when entering a vessel by using a bent endoscope tip. Especially, the endoscope tip can be arranged near a stone in the kidney by using the optical vision device.

The endoscope comprises an optical distance measuring device not shown in the figure at its tip, e.g. using propagation time measurements of light emitted and reflected at the stone.

Magnetic tracking system 3 enables a determination of the position of a magnetic coil in the endoscope tip as in the first embodiment. Under consideration of the residual distance to the stone measured, the focus region of shock wave apparatus 2 can be adjusted correctly. It is to be noted herein that magnetic tracking systems do not only deliver three dimensional position information but also direction information so that also the direction in which the distance has been measured by the distance measuring device can be known principally. However, approximations also can be used in case of small residual distances.

Further, endoscope 5 can comprise a catheter being displaced up to the stone together with a magnetic coil integrated therein. In this case, the distance measuring device is not necessary.

Figure 3:
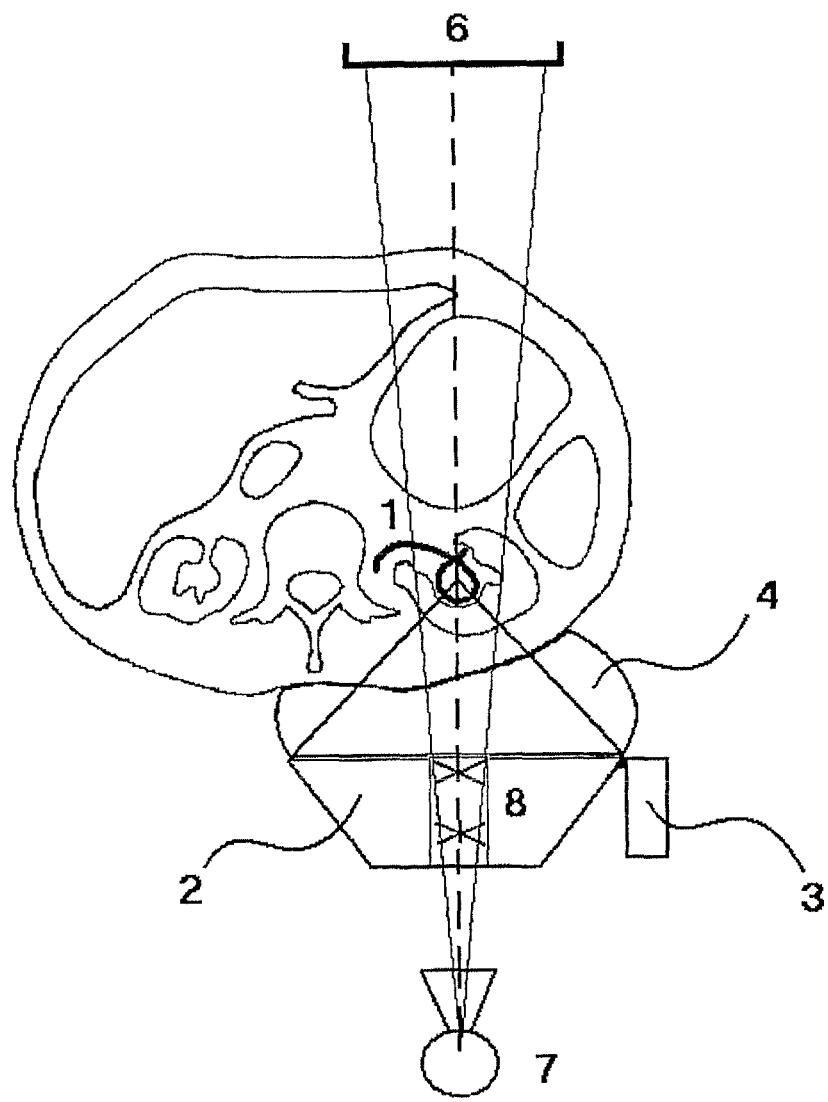
FIG. 3 shows a similar view as in FIG. 1, however of a third embodiment.

The third embodiment of FIG. 3 is an advantageous combination with X-ray imaging in a direction as in FIG. 1. Therein, the fact can be used that the focus region of shock wave apparatus 2 has a lengthy shape, i.e. is, in relation to the drawing, longer in a vertical manner than in a horizontal manner perpendicular to the plane of drawing. Thus, it is preliminarily desired to determine the position of the stone or the magnetic coil in a plane being inclined as minimally as possible relative to a plane perpendicular to the plane of drawing and intersecting this plane horizontally. Especially advantageous is the use of an X-ray apparatus coaxial to shock wave apparatus 2 which X-ray apparatus is shown in FIG. 3 additionally to FIG. 1.

Shock wave apparatus 2, especially the source, is arranged in the path of rays of X-ray system 6, 7 or arranged around it. The X-ray system is shown only schematically and comprises an X-ray source 7 on the, in relation to the body, distal side of shock wave apparatus 2 and an image amplifier 6 on the side of the body opposed to shock wave apparatus 2. Shock wave apparatus 2 has a hollow construction showing a central axial hole. This can be achieved by a hollow coil construction of the source. In the hollow hole, crosshair-like X-ray absorbing markers numerated with 8 and only schematically shown in the figure are arranged. Thereby, the complete construction of shock wave apparatus 2, X-ray apparatus 6, 7, and magnetic locating apparatus 3 can be oriented such that the stone and the magnetic coil are arranged in the crosshair or sufficiently near thereto. Alternatively, it can be sufficient to locate the stone in the X-ray image in some manner and to orientate the shock wave apparatus correspondingly, then. Herein, the X-ray apparatus needs not be moved as well.

This embodiment of the invention is especially adapted for indications in which a certain position of the treatment region, here the stone, and the catheter already results from anatomical conditions. For example, stones in the renal pelvis or at the end of a renal calice leading into the renal pelvis can have a varying position preliminarily in the longitudinal direction of the lengthy renal pelvis. Usually, the treatment is approximately perpendicular to this longitudinal direction. Thus, if it can be ascertained that the stone and the magnetic coil in the catheter are arranged correctly in an X-ray image as made in the above-mentioned direction, a positioning in the "depth" direction can be disposed with due to the anatomical situation. Namely, the renal pelvis can have an extension in this direction in the range of 2 cm whereas a typical focus region length of a shock wave apparatus can be in a range of 4 cm. Here, a two dimensional orientation by the X-ray image is sufficient. In the adjustment of the focus depth, it can be assumed that the magnetic coil is sufficiently near at the stone so that the treatment can be made without an additional reference localization by the magnetic tracking system. By detecting the position of the magnetic locating element in the imaging direction of the first X-ray image, a second X-ray image in a substantially different imaging direction can be avoided. This does not only reduce the X-ray load on the patient but also simplify the X-ray apparatus because tilting mechanisms are not necessary.

Incidentally, a combination with an ultrasonic imaging can be advantageous especially for the above-mentioned hollow construction of shock wave apparatus 2. The ultrasonic head can be moved through the hollow space and produce extracorporeal images that are alternative or additional to the X-ray image.

In addition, combinations of X-ray images with endoscopic visual controls are considered, especially if an X-ray imaging in only one imaging direction in the above-mentioned manner is desired for additional safety or for increasing the precision of the visual control whereas the latter is regarded to be sufficient for the third direction. In many practical cases, the visual control alone will be sufficient so that X-ray technology can be avoided completely.

The invention claimed is:

1. An apparatus for treating the human or animal body by focused shock waves, said apparatus comprising:
a shock wave source adapted to produce said shock waves,
a focusing device adapted to focus said shock waves onto a focus region in said body to be treated,
a locating probe adapted to be inserted into said body to be treated,
a magnetic locating element as a part of said locating probe and arranged in said locating probe, and
a magnetic locating apparatus adapted to locate said magnetic locating element in said body to be treated and thus adapted for navigation during said treatment.

2. The apparatus according to claim 1 wherein said locating probe is an endoscope having an optical vision device.

3. The apparatus according to claim 2 wherein said endoscope comprises a distance measuring device for measuring a distance between said endoscope and a region to be treated of said body.

4. The apparatus according to claim 3 wherein said distance measuring device is an optical distance measuring device.

5. The apparatus according to claim 2 wherein said endoscope comprises a catheter and said magnetic locating element is arranged within said catheter.

6. A method of using an apparatus according to claim 2 for navigation with regard to said region to be treated,
wherein said locating probe is inserted into said body and moved near said region to be treated,
wherein the distance between said magnetic locating element and said region to be treated is determined, and
wherein said magnetic locating element is located in said determined distance by means of said magnetic locating apparatus and is used for navigation monitoring of said region to be treated after said locating.

7. The method according to claim 6 wherein said region to be treated is located by means of an optical vision device of said endoscope and wherein said distance is determined after said locating.

8. The method according to claim 7 wherein said locating comprises a visual control by means of said optical vision device until said endoscope is arranged adjacent to said region to be treated.

9. The method according to claim 7 wherein said locating comprises a visual control by means of said optical vision device and a distance measurement of the distance between said endoscope and said region to be treated of said body.

10. The method according to claim 6 wherein said locating probe is detected in said determined distance between said magnetic locating element and said region to be treated of said body my means of an extracorporeal imaging by means of an extracorporeal imaging apparatus.

11. The method according to claim 10 wherein a catheter is moved until being adjacent to said region to be treated and said extracorporeal imaging of said region to be treated is conducted with said catheter being imaged, in order to determine said distance between said magnetic locating element and said region to be treated of said body.

12. The method according to claim 11 wherein an image axis of an X-ray apparatus and a main axis of a propagation of shock waves are coincident.

13. The method according to claim 12 wherein said position of said magnetic locating element along said axis of said X-ray apparatus is determined by means of said magnetic locating apparatus and in which X-ray imaging is contacted only with said coincident axis.

14. The method according to claim 6 in which said body is treated by shock waves focused to said region to be treated using a navigation by means of said magnetic locating element and said magnetic locating apparatus.

15. The apparatus according to claim 1 comprising an extracorporeal imaging apparatus adapted for producing images of said locating probe.

16. The apparatus according to claim 15 wherein said extracorporeal imaging apparatus is an X-ray apparatus.

17. The apparatus according to claim 15 wherein said extracorporeal imaging apparatus is adapted to be arranged coaxially to said shock wave source.

18. The apparatus according to claim 15 wherein said locating probe is a catheter.

19. The apparatus according to claim 1 wherein said shock wave source is arranged extracorporeally and is adapted to be coupled via a liquid volume to said body.

20. The apparatus according to claim 19 being a lithotripter.

21. The apparatus according to claim 1 wherein said locating element is a coil.

22. An apparatus for treating the human or animal body by focused shock waves, said apparatus comprising:
   an extra-corporeal shock wave source adapted to produce said shock waves,
   a focusing device integrated in said shock wave source and adapted to focus said shock waves onto a focus region in said body to be treated,
   a locating probe adapted to be inserted into said body to be treated,
   a magnetic locating element as a part of said locating probe and arranged in said locating probe, and
   a magnetic locating apparatus adapted to locate said magnetic locating element in said locating probe in said body to be treated and thus adapted for navigation during said treatment.

23. The apparatus according to claim 22 wherein said locating probe is an endoscope or a catheter.

24. The apparatus according to claim 22 wherein said magnetic locating element is selected from the group consisting of an active coil and a passive coil.

25. The apparatus according to claim 23 wherein said magnetic locating element is selected from the group consisting of an active coil and a passive coil.

* * * * *